(12) United States Patent
Takaishi et al.

(10) Patent No.: US 8,846,566 B2
(45) Date of Patent: Sep. 30, 2014

(54) COMPOSITION FOR CONTROLLING PLANT DISEASES AND METHOD FOR CONTROLLING PLANT DISEASES

(75) Inventors: Masanao Takaishi, Toyonaka (JP); Masato Soma, Narashino (JP)

(73) Assignee: Sumitomo Chemical Company, Limited, Tokyo (JP)

(*) Notice: Subject to any disclaimer, the term of this patent is extended or adjusted under 35 U.S.C. 154(b) by 39 days.

(21) Appl. No.: 13/130,571

(22) PCT Filed: Nov. 20, 2009

(86) PCT No.: PCT/JP2009/070073
§ 371 (c)(1),
(2), (4) Date: Jul. 25, 2011

(87) PCT Pub. No.: WO2010/061940
PCT Pub. Date: Jun. 3, 2010

(65) Prior Publication Data
US 2011/0269623 A1 Nov. 3, 2011

(30) Foreign Application Priority Data

Nov. 25, 2008 (JP) ................................. 2008-299272

(51) Int. Cl.
  *A01N 37/38* (2006.01)
  *A01N 43/653* (2006.01)
  *A01P 3/00* (2006.01)
  *A01N 55/00* (2006.01)

(52) U.S. Cl.
  CPC .............. *A01N 43/653* (2013.01); *A01N 37/38* (2013.01); *A01N 55/00* (2013.01)
  USPC ........ 504/100; 514/63; 514/266.23; 514/383; 514/384; 514/622

(58) Field of Classification Search
  USPC .............. 514/383, 617, 622, 63, 263.23, 384; 504/100
  See application file for complete search history.

(56) References Cited

U.S. PATENT DOCUMENTS

| | | | | |
|---|---|---|---|---|
| 4,938,792 A * | 7/1990 | Kumazawa et al. | .......... | 504/272 |
| 5,476,868 A | 12/1995 | Wingert et al. | | |
| 5,532,260 A | 7/1996 | Wingert et al. | | |
| 5,587,365 A | 12/1996 | Wingert et al. | | |
| 5,948,819 A | 9/1999 | Ohtsuka et al. | | |
| 6,313,150 B1 | 11/2001 | Ohtsuka et al. | | |
| 6,369,090 B1 | 4/2002 | Schelberger et al. | | |
| 6,689,356 B1 | 2/2004 | Zlotkin et al. | | |
| 6,746,988 B2 * | 6/2004 | Hopkinson et al. | .......... | 504/127 |
| 8,173,599 B2 | 5/2012 | Moon et al. | | |
| 8,232,229 B2 | 7/2012 | Arthur et al. | | |
| 2005/0043176 A1 | 2/2005 | Forster | | |
| 2005/0101639 A1 | 5/2005 | Ammermann et al. | | |
| 2008/0125318 A1 | 5/2008 | Gewehr et al. | | |
| 2008/0269051 A1 | 10/2008 | Suty-Heinze et al. | | |
| 2009/0325802 A1 | 12/2009 | Forster et al. | | |

FOREIGN PATENT DOCUMENTS

| | | |
|---|---|---|
| CN | 1409595 | 4/2003 |
| CN | 1951191 | 4/2007 |
| EP | 0353191 A2 | 1/1990 |
| EP | 0374753 A2 | 6/1990 |
| EP | 0392225 A2 | 10/1990 |
| EP | 0427529 A1 | 5/1991 |
| EP | 0451878 A1 | 10/1991 |
| EP | 0645091 A1 | 3/1995 |
| EP | 1183948 A1 | 6/1999 |
| EP | 1183948 A | 3/2002 |
| GB | 2315218 A | 1/1998 |
| WO | 93/07278 A1 | 4/1993 |
| WO | 95/27693 A1 | 10/1995 |
| WO | 95/33818 A2 | 12/1995 |
| WO | 95/34656 A1 | 12/1995 |
| WO | 03/045150 A2 | 11/2002 |
| WO | 03/000906 A2 | 1/2003 |
| WO | 03/052073 A2 | 6/2003 |
| WO | WO 03/045150 A | 6/2003 |

OTHER PUBLICATIONS

CABA abstract 1993:125699 (1993).*
CABA abstract 1999:76927 (1999).*
EPA Pesticide Fact Sheet: Ipconazole (2004).*
HCAPLUS abstract 1999:80709 (1999).*
"The Pesticide Manual—14th edition" published by British Crop Production Council, ed. C.D.S. Tomlin, 2006, ISBN:1901396142, pp. 121, 263, 323, 430, 503, 566, 596, 613, 689, 736, 895, 953, 1007, and 1088, Hampshire, United Kingdom.
Proceedings of the National Academy of Sciences USA, Sep. 1990, vol. 87, No. 17, pp. 7175-7179, Washington, DC, USA.
Weed Science, ed. Robert E. Blackshaw, Sep.-Oct. 2005, vol. 53, No. 5, pp. 728-746, Lawrence, Kansas, USA.
Trisha Gura: "Repairing the Genome's Spelling Mistakes," SCIENCE, American Association for the Advancement of Science, Jul. 16, 1999, vol. 285, pp. 316-318.
Communication: International Search Report for International Patent Application No. PCT/JP2009/070073 mailed Jul. 6, 2010.
Chinese Office Action for corresponding Chinese Application No. 200980146624.1 dated Oct. 25, 2012.

(Continued)

Primary Examiner — John Pak

(57) ABSTRACT

PROBLEM
There are provided a composition for controlling plant diseases and a method for controlling plant diseases having excellent control effect for plant diseases.
SOLUTION
A composition for controlling plant diseases comprising, as active ingredients, a compound represented by formula (1), wherein $X^1$ represents a methyl group, a difluoromethyl group or an ethyl group; $X^2$ represents a methoxy group or a methylamino group; and $X^3$ represents a phenyl group, a 2-methylphenyl group or a 2,5-dimethylphenyl group, and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole.

7 Claims, No Drawings

(56) References Cited

OTHER PUBLICATIONS

Chinese Office Action mailed May 16, 2013 in corresponding Chinese Application No. 200980146624.1.

Japanese Office Action for JP Application No. 2008-299272 mailed May 28, 2013.

Russian Office Action for RU Application No. 2011126121/13 mailed Sep. 2, 2013.

Ichiba, et al., Journal of Pesticide Science, vol. 27(2), 2002, pp. 118-126.

Office Action from corresponding UA Application No. a 2011 08015.

* cited by examiner

COMPOSITION FOR CONTROLLING PLANT DISEASES AND METHOD FOR CONTROLLING PLANT DISEASES

CROSS-REFERENCE TO RELATED APPLICATIONS

This application is a national stage of PCT/JP2009/070073, filed on Nov. 20, 2009, which claims priority to Japanese Patent Application No. 2008-299272, filed on Nov. 25, 2008. Each of these documents is incorporated herein by reference in its entirety.

TECHNICAL FIELD

The present invention relates to a composition for controlling plant diseases and a method for controlling plant diseases.

BACKGROUND ART

α-Substituted phenylacetic acid compounds (see, for example, Patent Document 1) and azole compounds (see, for example, Non-Patent Document 1) are conventionally known as active ingredients of agents for controlling plant diseases. Nevertheless, there is a continuing need for more highly active agents for controlling plant diseases.
Patent Document 1: WO 95/27,693
Non-Patent Document 1: "The Pesticide Manual-14th edition" published by BCPC, ISBN: 1901396142

DISCLOSURE OF THE INVENTION

Problems to be Solved by the Invention

An object of the present invention is to provide a composition for controlling plant diseases and a method for controlling plant diseases, having excellent control effect for plant diseases, and so on.

Means for Solving the Problems

The present invention provides a composition for controlling plant diseases and a method for controlling plant diseases, having an improved control effect for plant diseases by combining a compound represented by the following formula (1) with a specific azole compound.
Specifically, the present invention takes the following constitutions.
[1] A composition for controlling plant diseases comprising, as active ingredients, a compound represented by formula (1):

[Formula 1]

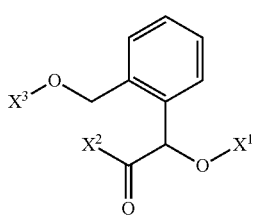

(1)

wherein $X^1$ represents a methyl group, a difluoromethyl group or an ethyl group; $X^2$ represents a methoxy group or a methylamino group; and $X^3$ represents a phenyl group, a 2-methylphenyl group or a 2,5-dimethylphenyl group;
and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole;
[2] The composition according to [1], wherein the azole compound is at least one azole compound selected from the group consisting of bromuconazole, difenoconazole, fluquinconazole, ipconazole, prothioconazole, tetraconazole, triticonazole and metconazole;
[3] The composition according to [1] or [2], which has a weight ratio of the compound represented by formula (1) to the at least one azole compound falling within the range of from 0.0125:1 to 500:1;
[4] A seed treatment agent comprising, as active ingredients, the compound represented by formula (1) of [1] and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole;
[5] A plant seed treated with effective amounts of the compound represented by formula (1) of [1] and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole;
[6] A method for controlling plant diseases which comprises applying, to a plant or a locus where a plant is allowed to grow, effective amounts of the compound represented by formula (1) of [1] and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole; and
[7] Combined use for controlling plant diseases of the compound represented by formula (1) of [1] and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole; and so on.

Advantage of the Invention

The composition according to the present invention exhibits an excellent control effect for plant diseases.

BEST MODE FOR CARRYING OUT THE INVENTION

The compound represented by formula (1) for use in the composition for controlling plant diseases according to the present invention is described.
Examples of the compound represented by formula (1) includes the following compounds.
A compound in which $X^1$ is a methyl group, a difluoromethyl group or an ethyl group in formula (1);
a compound in which $X^1$ is a methyl group in formula (1);
a compound in which $X^2$ is a methoxy group or a methylamino group in formula (1);

a compound in which $X^1$ is a methyl group and $X^2$ is a methoxy group in formula (1);

a compound in which $X^1$ is a methyl group and $X^2$ is methylamino group in formula (1);

a compound in which $X^3$ is a phenyl group, a 2-methylphenyl group or a 2,5-dimethylphenyl group in formula (1);

a compound in which $X^3$ is a phenyl group or a 2,5-dimethylphenyl group in formula (1);

a compound in which $X^1$ is a methyl group, $X^2$ is a methoxy group, and $X^3$ is a 2,5-dimethylphenyl group in formula (1);

a compound in which $X^1$ is a methyl group, is methylamino group, and $X^3$ is a phenyl group in formula (1); and a compound in which $X^1$ is a methyl group, $X^2$ is methylamino group, and $X^3$ is a 2,5-dimethylphenyl group in formula (1).

Next, specific examples of the compound represented by formula (1) are shown.

In the compound represented by formula (1), $X^1, X^2, X^3$ are one of the combinations of substituents shown in Table 1.

TABLE 1

| $X^1$ | $X^2$ | $X^3$ |
|---|---|---|
| $CH_3$ | $OCH_3$ | Ph |
| $CH_3$ | $OCH_3$ | $2\text{-}CH_3Ph$ |
| $CH_3$ | $OCH_3$ | $2,5\text{-}(CH_3)_2Ph$ |
| $CH_3$ | $NHCH_3$ | Ph |
| $CH_3$ | $NHCH_3$ | $2\text{-}CH_3Ph$ |
| $CH_3$ | $NHCH_3$ | $2,5\text{-}(CH_3)_2Ph$ |
| $CHF_2$ | $OCH_3$ | Ph |
| $CHF_2$ | $OCH_3$ | $2\text{-}CH_3Ph$ |
| $CHF_2$ | $OCH_3$ | $2,5\text{-}(CH_3)_2Ph$ |
| $CHF_2$ | $NHCH_3$ | Ph |
| $CHF_2$ | $NHCH_3$ | $2\text{-}CH_3Ph$ |
| $CHF_2$ | $NHCH_3$ | $2,5\text{-}(CH_3)_2Ph$ |
| $C_2H_5$ | $OCH_3$ | Ph |
| $C_2H_5$ | $OCH_3$ | $2\text{-}CH_3Ph$ |
| $C_2H_5$ | $OCH_3$ | $2,5\text{-}(CH_3)_2Ph$ |
| $C_2H_5$ | $NHCH_3$ | Ph |
| $C_2H_5$ | $NHCH_3$ | $2\text{-}CH_3Ph$ |
| $C_2H_5$ | $NHCH_3$ | $2,5\text{-}(CH_3)_2Ph$ |

The compound represented by formula (1) may have isomers such as stereoisomers such as optical isomers based on an asymmetric carbon atoms and tautomers, and any isomer can be contained and used solely or in a mixture of any isomer ratio in the present invention.

The compound represented by formula (1) may be in a form of a solvate (for example, hydrate) and it can be used in a form of a solvate in the present invention.

The compound represented by formula (1) may be in a form of a crystal form and/or an amorphous form and it can be used in any form in the present invention.

The compound represented by formula (1) is a compound described in WO95/27,693 pamphlet. These compounds can be synthesized, for example, by a method described in the pamphlet.

Next, the azole compound for use in the composition for controlling plant diseases according to the present invention in combination with the compound represented by formula (1) is at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole. All of the azole compounds included in this group are well-known compounds, such as those described in "The Pesticide Manual-14th edition" published by BCPC, ISBN: 1901396142, pp. 121, 263, 323, 430, 503, 566, 596, 613, 736, 895, 953, 1007, 1088, and 689. These compounds can be obtained from commercial agents or prepared using well-known methods. The azole compound is preferably bromuconazole, difenoconazole, fluquinconazole, ipconazole, prothioconazole, tetraconazole, triticonazole and metconazole.

In the composition for controlling plant diseases according to the present invention, the weight ratio of the compound represented by formula (1) to the azole compound, for example, any of bromuconazole, difenoconazole, fluquinconazole, ipconazole, prothioconazole, tetraconazole, triticonazole and metconazole is typically in the range of 0.0125:1 to 500:1, preferably 0.025:1 to 100:1. In addition, when used as a dusting powder, the range of 0.025:1 to 40:1 is more preferable, and when used as a seed treatment agent, the range of 0.25:1 to 100:1 is more preferable.

The composition for controlling plant diseases according to the present invention may be a simple mixture of the compound represented by formula (1) and the azole compound. Alternatively, the composition for controlling plant diseases is typically produced by mixing the compound represented by formula (1) and the azole compound with an inert carrier, and adding to the mixture a surfactant and other adjuvants as needed so that the mixture can be formulated into an oil agent, an emulsion, a flowable agent, a wettable powder, a granulated wettable powder, a powder agent, a granule agent and so on. The composition for controlling plant diseases mentioned above can be used as a seed treatment agent of the present invention as it is or added with other inert ingredients.

In the composition for controlling plant diseases according to the present invention, the total amount of the compound represented by formula (1) and the azole compound, for example, any of bromuconazole, difenoconazole, fluquinconazole, ipconazole, prothioconazole, tetraconazole, triticonazole and metconazole is typically in the range of 0.1 to 99% by weight, preferably 0.2 to 90% by weight.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; and nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

The composition for controlling plant diseases according to the present invention is effective for the following plant diseases.

Diseases of rice: blast (*Magnaporthe grisea*), Helminthosporium leaf spot (*Cochliobolus miyabeanus*), sheath blight (*Rhizoctonia solani*), and bakanae disease (*Gibberella fujikuroi*).

Diseases of wheat: powdery mildew (*Erysiphe graminis*), Fusarium head blight (*Fusarium graminearum, F. avenacerum, F. culmorum, Microdochium nivale*), rust (*Puccinia striiformis, P. graminis, P. recondita*), pink snow mold (*Micronectriella nivale*), Typhula snow blight (*Typhula sp.*), loose smut (*Ustilago tritici*), bunt (*Tilletia caries*), eyespot (*Pseudocercosporella herpotrichoides*), leaf blotch (*Mycosphaerella graminicola*), glume blotch (*Stagonopospora nodorum*), and yellow spot (*Pyrenophora tritici-repentis*).

Diseases of barley: powdery mildew (*Erysiphe graminis*), Fusarium head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and Rhizoctonia damping-off (*Rhizoctonia solani*).

Diseases of corn: smut (*Ustilago maydis*), brown spot (*Cochliobolus heterostrophus*), copper spot (*Gloeocercospora sorghi*), southern rust (*Puccinia polysora*), gray leaf spot (*Cercospora zeae-maydis*), and Rhizoctonia damping-off (*Rhizoctonia solani*).

Diseases of citrus: melanose (*Diaporthe citri*), scab (*Elsinoe fawcetti*), penicillium rot (*Penicillium digitatum, P. italicum*), and brown rot (*Phytophthora parasitica, Phytophthora citrophthora*).

Diseases of apple: blossom blight (*Monilinia mali*), canker (*Valsa ceratosperma*), powdery mildew (*Podosphaera leucotricha*), Alternaria leaf spot (*Alternaria alternata* apple pathotype), scab (*Venturia inaequalis*), bitter rot (*Colletotrichum acutatum*), crown rot (*Phytophtora cactorum*), blotch (*Diplocarpon mali*), and ring rot (*Botryosphaeria berengeriana*).

Diseases of pear: scab (*Venturia nashicola, V. pirina*), black spot (*Alternaria alternata* Japanese pear pathotype), rust (*Gymnosporangium haraeanum*), and *phytophthora* fruit rot (*Phytophtora cactorum*);

Diseases of peach: brown rot (*Monilinia fructicola*), scab (*Cladosporium carpophilum*), and *phomopsis* rot (*Phomopsis sp.*).

Diseases of grape: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*).

Diseases of Japanese persimmon: anthracnose (*Gloeosporium kaki*), and leaf spot (*Cercospora kaki, Mycosphaerella nawae*).

Diseases of gourd: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora rot (*Phytophthora sp.*), damping-off (*Pythium sp.*) and Rhizoctonia damping-off (*Rhizoctonia solani*);

Diseases of tomato: early blight (*Alternaria solani*), leaf mold (*Cladosporium fulvum*), and late blight (*Phytophthora infestans*).

Diseases of eggplant: brown spot (*Phomopsis vexans*), and powdery mildew (*Erysiphe cichoracearum*).

Diseases of cruciferous vegetables: Alternaria leaf spot (*Alternaria japonica*), white spot (*Cercosporella brassicae*), clubroot (*Plasmodiophora brassicae*), and downy mildew (*Peronospora parasitica*).

Diseases of welsh onion: rust (*Puccinia allii*), and downy mildew (*Peronospora destructor*).

Diseases of soybean: purple seed stain (*Cercospora kikuchii*), sphaceloma scad (*Elsinoe glycines*), pod and stem blight (*Diaporthe phaseolorum* var. *sojae*), septoria brown spot (*Septoria glycines*), frogeye leaf spot (*Cercospora sojina*), rust (*Phakopsora pachyrhizi*), brown stem rot (*Phytophthora sojae*), and Rhizoctonia damping-off (*Rhizoctonia solani*).

Diseases of kidney bean: anthracnose (*Colletotrichum lindemthianum*).

Diseases of peanut: leaf spot (*Cercospora personata*), brown leaf spot (*Cercospora arachidicola*) and southern blight (*Sclerotium rolfsii*).

Diseases of garden pea: powdery mildew (*Erysiphe pisi*), and root rot (*Fusarium solani* f. sp. *pisi*).

Diseases of potato: early blight (*Alternaria solani*), late blight (*Phytophthora infestans*), pink rot (*Phytophthora erythroseptica*), and powdery scab (*Spongospora subterranean* f. sp. *subterranea*).

Diseases of strawberry: powdery mildew (*Sphaerotheca humuli*), and anthracnose (*Glomerella cingulata*).

Diseases of tea: net blister blight (*Exobasidium reticulatum*), white scab (*Elsinoe leucospila*), gray blight (*Pestalotiopsis sp.*), and anthracnose (*Colletotrichum theae-sinensis*).

Diseases of tobacco: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*).

Diseases of rapeseed: sclerotinia rot (*Sclerotinia sclerotiorum*), and Rhizoctonia damping-off (*Rhizoctonia solani*).

Diseases of cotton: Rhizoctonia damping-off (*Rhizoctonia solani*).

Diseases of sugar beat: *Cercospora* leaf spot (*Cercospora beticola*), leaf blight (*Thanatephorus cucumeris*), Root rot (*Thanatephorus cucumeris*), and Aphanomyces root rot (*Aphanomyces cochlioides*).

Diseases of rose: black spot (*Diplocarpon rosae*), powdery mildew (*Sphaerotheca pannosa*), and downy mildew (*Peronospora sparsa*).

Diseases of chrysanthemum and asteraceous plants: downy mildew (*Bremia lactucae*), leaf blight (*Septoria chrysanthemi-indici*), and white rust (*Puccinia horiana*).

Diseases of various groups: diseases caused by *Pythium* spp. (*Pythium aphanidermatum, Pythium debarianum, Pythium graminicola, Pythium irregulare, Pythium ultimum*), gray mold (*Botrytis cinerea*), and Sclerotinia rot (*Sclerotinia sclerotiorum*).

Disease of Japanese radish: Alternaria leaf spot (*Alternaria brassicicola*).

Diseases of turfgrass: dollar spot (*Sclerotinia homeocarpa*), and brown patch and large patch (*Rhizoctonia solani*).

Disease of banana: sigatoka (*Mycosphaerella fijiensis, Mycosphaerella musicola*).

Disease of sunflower: downy mildew (*Plasmopara halstedii*).

Seed diseases or diseases in the early stages of the growth of various plants caused by bacteria of *Aspergillus* genus, *Penicillium* genus, *Fusarium* genus, *Gibberella* genus, *Trico-*

*derma* genus, *Thielaviopsis* genus, *Rhizopus* genus, *Mucor* genus, *Corticium* genus, *Phoma* genus, *Rhizoctonia* genus and *Diplodia* genus.

Viral diseases of various plants mediated by *Polymixa* genus or the *Olpidium* genus and so on.

Plant diseases can be controlled by applying effective amounts of the compound represented by formula (1) and the azole compound(s) to the plant pathogens or a place where the plant pathogens inhabit or a place (plant, soil) where the plant pathogens may inhabit.

Plant diseases can be controlled by applying effective amounts of the compound represented by formula (1) and the azole compound(s) to a plant or a place where a plant is allowed to grow. As a plant which is the object of application, stalk and leaves of the plant, seed of the plant, bulbs of the plant can be included. Here, the bulb means a bulb, corm, rhizoma, stem tuber, root tuber and rhizophore.

When the application is conducted to plant diseases, a plant or the soil where the plant is allowed to grow, the compound represented by formula (1) and the azole compound(s) may be separately applied for the same period, but they are typically applied as a composition for controlling plant diseases of the present invention from the viewpoint of simplicity of the application.

The controlling method of the present invention includes treatment of stalk and leaves of a plant, treatment of the place where the plant is allowed to grow such as the soil, treatment of the seeds such as seed sterilization/seed coating and treatment of the bulb such as potato sets.

As the treatment of stalk and leaves of a plant in the control method of the present invention, specifically, for example, application onto the surface of the plant such as spraying to the stalk and leaves and spraying to the trunk can be included.

As the treatment of the soil in the control method of the present invention, for example, spraying onto the soil, admixing with the soil, perfusion of an agent liquid into the soil (irrigation of an agent liquid, injection into the soil, dripping of an agent liquid) can be included and the examples of the place to be treated include a planting hole, a furrow, peripheral of the planting hole, peripheral of the planting furrow, the entire surface of the growing area, the parts between the soil and the plant, area between roots, area beneath the trunk, main furrow, growing soil, box for raising seedlings, tray for raising seedlings, seedbed. The treatment can be performed before dissemination, at the time of dissemination, immediately after the dissemination, during the raising period of seedlings, before settled planting, at the time of settled planting and growing time after settled planting. In the soil treatment mentioned above, the active ingredients may be applied to the plant at the same time, or solid manure such as paste manure containing the active ingredients may be applied to the soil. The active ingredients may be mixed in irrigating liquid, and, for example, may be injected to irrigating facilities (irrigating tube, irrigating pipe, sprinkler, etc.), mixed into the flooding liquid between furrows, or mixed into a water culture medium. Alternatively, the irrigating liquid and the active ingredients may be mixed beforehand and, for example, used for treatment by an appropriate irrigating method including the irrigating method mentioned above and the other methods such as sprinkling and flooding.

Treatment of a seed in the control method of the present invention is, for example, a method for treating a seed, a bulb or the like to be protected from plant diseases with a composition for controlling plant diseases of the present invention and specific examples thereof include a spraying treatment in which a suspension of the composition for controlling plant diseases of the present invention is atomized and sprayed on the seed surface or the bulb surface; smearing treatment in which a wettable powder, an emulsion, a flowable agent or the like of the composition for controlling plant diseases of the present invention as it is or added with a small amount of water is applied on the seed surface or the bulb surface; immersing treatment in which the seed is immersed in a solution of the composition for controlling plant diseases of the present invention for a certain period of time; film coating treatment and pellet coating treatment.

When a plant or the soil for growing a plant is treated with the compound represented by formula (1) and the azole compound, for example, any of bromuconazole, difenoconazole, fluquinconazole, ipconazole, prothioconazole, tetraconazole, triticonazole and metconazole, the amount for the treatment may be changed depending on the kind of the plant to be treated, the kind and the occurring frequency of the diseases to be controlled, formulation form, treatment period, climatic condition and so on, but the total amount of the compound represented by formula (1) and the azole compound (hereinbelow referred to as the amount of the active ingredients) per 10,000 m$^2$ is typically 1 to 5000 g and preferably 2 to 200 g.

The emulsion, wettable powder, flowable agent or the like is typically diluted with water, and then sprinkled for treatment. In this case, the concentration of the active ingredients is typically in the range of 0.0001 to 3% by weight and preferably 0.0005 to 1% by weight. The powder agent, granule agent or the like is typically used for treatment without dilution.

In the treatment of seeds, the amount of the applied active ingredients is typically in the range of 0.001 to 20 g, preferably 0.01 to 5 g per 1 kg of seeds.

The control method of the present invention can be used in agricultural lands such as fields, paddy fields, lawns and orchards or in non-agricultural lands.

The present invention can be used to control diseases in agricultural lands for cultivating the following "plant" and the like without adversely affecting the plant and so on.

Examples of the crops are as follows:

crops: corn, rice, wheat, barley, rye, oat, sorghum, cotton, soybean, peanut, buckwheat, beet, rapeseed, sunflower, sugar cane, tobacco, etc.;

vegetables: solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, *Dioscorea japonica*, colocasia, etc., flowers, foliage plants, turf grasses, fruits: pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, lemon, rime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, kaki fruit, olive, Japanese plum, banana, coffee, date palm, coconuts, etc., trees other than fruit trees; tea, mulberry, flowering plant, roadside trees (ash, birch, dogwood, *Eucalyptus, Ginkgo biloba*, lilac, maple, *Quercus*, poplar, Judas tree, *Liquidam-*

*bar formosana*, plane tree, zelkova, Japanese arborvitae, fir wood, hemlock, juniper, *Pinus, Picea*, and *Taxus cuspidate*), etc.

The aforementioned "plants" include plants, to which resistance to HPPD inhibitors such as isoxaflutole, ALS inhibitors such as imazethapyr or thifensulfuron-methyl, EPSP synthetase inhibitors such as glyphosate, glutamine synthetase inhibitors such as the glufosinate, acetyl-CoA carboxylase inhibitors such as sethoxydim, PPO inhibitors such as flumioxazin, and herbicides such as bromoxynil, dicamba, 2,4-D, etc. has been conferred by a classical breeding method or genetic engineering technique.

Examples of a "plant" on which resistance has been conferred by a classical breeding method include rape, wheat, sunflower and rice resistant to imidazolinone ALS inhibitory herbicides such as imazethapyr, which are already commercially available under a product name of Clearfield (registered trademark). Similarly, there is soy bean on which resistance to sulfonylurea ALS inhibitory herbicides such as thifensulfuron-methyl has been conferred by a classical breeding method, which is already commercially available under a product name of STS soy bean. Similarly, examples on which resistance to acetyl-CoA carboxylase inhibitors such as trione oxime or aryloxy phenoxypropionic acid herbicides has been conferred by a classical breeding method include SR corn. The plant on which resistance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase resistant to an acetyl-CoA carboxylase inhibitor is reported in Weed Science, vol. 53, pp. 728-746 (2005) and a plant resistant to acetyl-CoA carboxylase inhibitors can be generated by introducing a gene of such an acetyl-CoA carboxylase variation into a plant by genetically engineering technology, or by introducing a variation conferring resistance into a plant acetyl-CoA carboxylase. Furthermore, plants resistant to acetyl-CoA carboxylase inhibitors or ALS inhibitors or the like can be generated by introducing a site-directed amino acid substitution variation into an acetyl-CoA carboxylase gene or the ALS gene of the plant by introduction a nucleic acid into which has been introduced a base substitution variation represented Chimeraplasty Technique (Gura T. 1999. Repairing the Genome's Spelling Mistakes. Science 285: 316-318) into a plant cell.

Examples of a plant on which resistance has been conferred by genetic engineering technology include corn, soy bean, cotton, rape, sugar beet resistant to glyphosate, which is already commercially available under a product name of RoundupReady (registered trademark), AgrisureGT, etc. Similarly, there are corn, soy bean, cotton and rape which are made resistant to glufosinate by genetic engineering technology, a kind, which is already commercially available under a product name of LibertyLink (registered trademark). A cotton made resistant to bromoxynil by genetic engineering technology is already commercially available under a product name of BXN likewise.

The aforementioned "plants" include genetically engineered crops produced using such genetic engineering techniques, which, for example, are able to synthesize selective toxins as known in genus *Bacillus*.

Examples of toxins expressed in such genetically engineered crops include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3, or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Moreover, toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, etc.

Toxins contained in such genetically engineered plants are able to confer resistance particularly to insect pests belonging to Coleoptera, Hemiptera, Diptera, Lepidoptera and Nematodes, to the plants.

Furthermore, genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing phosphinotricine N-acetyl transferase (PAT) so as to confer resistance to Cry1Fa2 toxin and glufosinate), NuCOTN33B (registered trademark) (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-resistant trait), Agrisure (registered trademark) CB Advantage (Bt11 corn borer (CB) trait), and Protecta (registered trademark).

The aforementioned "plants" also include crops produced using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and antipathogenic substances generated by microorganisms, such as a peptide antibiotic, an antibiotic having a hetero ring, a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, etc.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soy bean having reduced linolenic content) or high-lysine (high-oil) corn (corn with increased lysine or oil content).

Furthermore, stack varieties are also included in which a plurality of advantageous characters such as the classic herbicide characters mentioned above or herbicide tolerance genes, insecticidal harmful insect resistance genes, antipathogenic substance producing genes, characters improved in oil stuff ingredients or characters having reinforced amino acid content are combined.

In the case of spray treatment, a high control effect is expected in particular for plant diseases which occur in wheat, citrus, soy bean, kidney bean, cotton, rapeseed, grape, turfgrass, pear, peach, apple, peanut, tea, sugar beet, banana, rice or gourd among the above. Examples of which a particularly high control effect of the present invention is expected for plant diseases among the diseases which occur in these plants include pink snow mold (*Microdochium nivale*), Rhizoctonia damping-off (*Rhizoctonia solani*), Fusarium head blight (*Fusarium graminearum, F. avenacerum, F. culmorum, Microdochium nivale*) and eyespot (*Pseudocercosporella herpotrichoides*) of wheat, diseases of citrus; melanose (*Diaporthe citri*) and scab (*Elsinoe fawcetti*), purple seed stain (*Cercospora kikuchii*), rust (*Phakopsora pachyrhizi*) of soybean, Rhizoctonia damping-off (*Rhizoctonia solani*) of cotton, Rhizoctonia damping-off (*Rhizoctonia solani*) and sclerotinia rot (*Sclerotinia sclerotiorum*) of rapeseed, anthracnose (*Elsinoe ampelina*), ripe rot (*Glomerella cingulata*), powdery mildew (*Uncinula necator*), black rot (*Guignardia bidwellii*) and gray mold (*Botrytis cinerea*) of grape, dollar spot (*Sclerotinia homeocarpa*) and brown patch (*Rhizoctonia solani*) of turfgrass, scab (*Venturia nashicola, V. pirina*) of pear, blossom blight (*Monilinia mali*), scab (*Venturia inaequalis*), powdery mildew (*Podosphaera leucotricha*), blotch (*Diplocarpon mali*) and ring rot (*Botryosphaeria berengeriana*) of apple, brown rot (*Monilinia fructicola*) and phomopsis rot (*Phomopsis sp.*) of peach, early leaf spot (*Cercospora arachidicola*) of peanut, gray blight (*Pestalotiopsis sp.*) and anthracnose (*Colletotrichum theaesinensis*) of tea, Cercospora leaf spot (*Cercospora beticola*), leaf blight (*Thanatephorus cucumeris*) and root rot (*Thanatephorus cucumeris*) of sugar beat, sigatoka (*Mycosphaerella fijiensis, Mycosphaerella musicola*) of banana, blast (*Magnaporthe grisea*) and bakanae disease (*Gibberella fujikuroi*) of rice, Rhizoctonia damping-off (*Rhizoctonia solani*) of gourd, gray mold (*Botrytis cinerea*) and Sclerotinia rot (*Sclerotinia sclerotiorum*) of the other crops.

In the case of seed treatment, a high control effect is expected in particular for plant diseases which occur in corn, sorghum, rice, rapeseed, soy bean, potato, sugar beet, cotton among the above. Among plant diseases occurring in these plants, plant diseases on which particularly high effects are expected include *Rhizoctonia* damping-off, diseases caused by *Pythium* spp. and diseases caused by *Fusarium* spp.

EXAMPLES

In the following, the present invention will be more specifically described by way of formulation examples, seed treatment formulation examples, and test examples. However, the present invention is not limited to the following examples. In the following examples, the part represents part by weight unless otherwise noted in particular.

The compound (1a) is a compound represented by formula (1) wherein $X^1$ is a methyl group, $X^2$ is a methylamino group, and $X^3$ is a 2,5-dimethylphenyl group and the compound has an R type steric structure according to Cahn-Ingold-Prelog order rule, and represented by the following formula (1a).

[Formula 2]

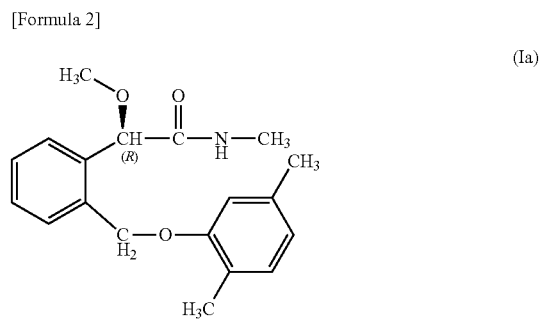

(Ia)

The compound (1b) is a compound represented by formula (1) wherein $X^1$ is a methyl group, $X^2$ is a methylamino group, and $X^3$ is a 2,5-dimethylphenyl group and the compound is an racemic body and represented by the following formula (1b).

[Formula 3]

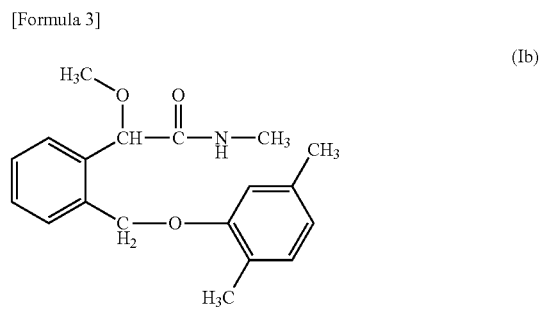

(Ib)

Formulation Example 1

2.5 Parts of the compound (1a) or the compound (1b), 1.25 parts of bromuconazole, 14 parts of polyoxyethylene styrylphenyl ether, 6 parts of calcium dodecyl benzene sulfonate and 76.25 parts of xylene are fully mixed, so as to obtain respective emulsions.

Formulation Example 2

5 Parts of the compound (1a) or the compound (1b), 5 parts of difenoconazole, 35 parts of a mixture of white carbon and a polyoxyethylene alkyl ether sulfate ammonium salt (weight ratio 1:1) and 55 parts of water are mixed, and the mixture is subjected to fine grinding according to a wet grinding method, so as to obtain respective flowable agents.

Formulation Example 3

5 Parts of the compound (1a) or the compound (1b), 10 parts of fluquinconazole, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain respective flowables.

Formulation Example 4

5 Parts of the compound (1a) or the compound (1b), 20 parts of prothioconazole, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain respective flowable formulations.

Formulation Example 5

40 Parts of the compound (1a) or the compound (1b), 5 parts of tetraconazole, 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. 150 parts of glass beads (diameter=1 mm) are put into 100 parts of the slurry, and the slurry is ground for 2 hours while being cooled with a cooling water. After ground, the resultant is filtered to remove the glass beads and respective flowables were obtained.

Formulation Example 6

50 Parts of the compound (1a) or the compound (1b), 0.5 part of triticonazole, 38.5 parts of NN kaolin clay (manufactured by Takehara Chemical Industrial), 10 parts of MorwetD425 and 1.5 parts of MorwerEFW (manufactured by Akzo Nobel Corp.) are mixed to obtain an AI premix. This premix was ground with a jet mill so as to obtain respective powders.

Formulation Example 7

1 Part of the compound (1a) or the compound (1b), 4 parts of bromuconazole, 1 part of synthetic hydrated silicon oxide, 2 parts of calcium lignin sulfonate, 30 parts of bentonite and 62 parts of kaolin clay are fully ground and mixed, and the resultant mixture is added with water and fully kneaded, and then subjected to granulation and drying so as to obtain respective granules.

Formulation Example 8

1 Part of the compound (1a) or the compound (1b), 40 parts of difenoconazole, 3 parts of calcium lignin sulfonate, 2 parts of sodium lauryl sulfate and 54 parts of synthetic hydrated silicon oxide are fully ground and mixed so as to obtain respective wettable powders.

Formulation Example 9

1 Part of the compound (1a) or the compound (1b), 2 parts of fluquinconazole, 85 parts of kaolin clay and 10 parts of talc are fully ground and mixed so as to obtain respective powders.

Formulation Example 10

2 Parts of the compound (1a) or the compound (1b), 0.25 part of prothioconazole, 14 parts of polyoxyethylene styrylphenyl ether, 6 parts of calcium dodecyl benzene sulfonate and 77.75 parts of xylene are fully mixed, so as to obtain respective emulsions.

Formulation Example 11

10 Parts of the compound (1a) or the compound (1b), 2.5 parts of tetraconazole, 1.5 parts of sorbitan trioleate, 30 parts of an aqueous solution containing 2 parts of polyvinyl alcohol are subjected to fine grinding according to a wet grinding method. Thereafter, 47.5 parts of an aqueous solution containing 0.05 part of Xanthan gum and 0.1 part of aluminum magnesium silicate is added to the ground solution, and 10 parts of propylene glycol is further added thereto. The obtained mixture is blended by stirring, so as to obtain respective flowables.

Formulation Example 12

1 Part of the compound (1a) or the compound (1b), 20 parts of triticonazole, 1 part of synthetic hydrated silicon oxide, 2 parts of calcium lignin sulfonate, 30 parts of bentonite and 47 parts of kaolin clay are ground and mixed, and the resultant mixture is added with water and fully kneaded, and then subjected granulation and drying so as to obtain respective granules.

Formulation Example 13

40 Parts of the compound (1a) or the compound (1b), 1 part of ipconazole, 3 parts of calcium lignin sulfonate, 2 parts of sodium lauryl sulfate and 54 parts of synthetic hydrated silicon oxide are fully ground and mixed so as to obtain respective wettable powders.

Formulation Example 14

5 Parts of the compound (1a) or the compound (1b), 1.25 parts of metconazole, 14 parts of polyoxyethylene styrylphenyl ether, 6 parts of calcium dodecyl benzene sulfonate and 76.25 parts of xylene are fully mixed, so as to obtain respective emulsions.

Formulation Example 15

5 Parts of the compound (1a) or the compound (1b), 5 parts of ipconazole, 35 parts of a mixture of white carbon and a polyoxyethylene alkyl ether sulfate ammonium salt (weight ratio 1:1) and 55 parts of water are mixed, and the mixture is subjected to fine grinding according to a wet grinding method, so as to obtain respective flowable agents.

Formulation Example 16

5 Parts of the compound (1a) or the compound (1b), 10 parts of metconazole, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain respective flowables.

Formulation Example 17

5 Parts of the compound (1a) or the compound (1b), 20 parts of ipconazole, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain respective flowable formulations.

Formulation Example 18

40 Parts of the compound (1a) or the compound (1b), 5 parts of metconazole, 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. 150 parts of glass beads (diameter=1 mm) are put into 100 parts of the slurry, and the slurry is ground for 2 hours while being cooled with a cooling water. After ground, the resultant is filtered to remove the glass beads and respective flowables were obtained.

Formulation Example 19a

50 Parts of the compound (1a) or the compound (1b), 0.5 part of ipconazole, 38.5 parts of NN kaolin clay (manufactured by Takehara Chemical Industrial), 10 parts of MorwetD425 and 1.5 parts of MorwerEFW (manufactured by Akzo Nobel Corp.) are mixed to obtain an AI premix. This premix was ground with a jet mill so as to obtain respective powders.

Formulation Example 19b

1 Part of the compound (1a) or the compound (1b), 4 parts of metconazole, 1 part of synthetic hydrated silicon oxide, 2 parts of calcium lignin sulfonate, 30 parts of bentonite and 62 parts of kaolin clay are fully ground and mixed, and the resultant mixture is added with water and fully kneaded, and then subjected to granulation and drying so as to obtain respective granules.

Formulation Example 20

1 Part of the compound (1a) or the compound (1b), 40 parts of ipconazole, 3 parts of calcium lignin sulfonate, 2 parts of sodium lauryl sulfate and 54 parts of synthetic hydrated silicon oxide are fully ground and mixed so as to obtain respective wettable powders.

Formulation Example 21

1 Part of the compound (1a) or the compound (1b), 2 parts of metconazole, 85 parts of kaolin clay and 10 parts of talc are fully ground and mixed so as to obtain respective powders.

Formulation Example 22

2 Parts of the compound (1a) or the compound (1b), 0.25 part of ipconazole, 14 parts of polyoxyethylene styrylphenyl ether, 6 parts of calcium dodecyl benzene sulfonate and 77.75 parts of xylene are fully mixed, so as to obtain respective emulsions.

Formulation Example 23

10 Parts of the compound (1a) or the compound (1b), 2.5 parts of metconazole, 1.5 parts of sorbitan trioleate, 30 parts of an aqueous solution containing 2 parts of polyvinyl alcohol are subjected to fine grinding according to a wet grinding method. Thereafter, 47.5 parts of an aqueous solution containing 0.05 part of Xanthan gum and 0.1 part of aluminum magnesium silicate is added to the ground solution, and 10 parts of propylene glycol is further added thereto. The obtained mixture is blended by stirring, so as to obtain respective flowables.

Formulation Example 24

1 Part of the compound (1a) or the compound (1b), 20 parts of ipconazole, 1 part of synthetic hydrated silicon oxide, 2 parts of calcium lignin sulfonate, 30 parts of bentonite and 47 parts of kaolin clay are ground and mixed, and the resultant mixture is added with water and fully kneaded, and then subjected granulation and drying so as to obtain respective granules.

Formulation Example 25

40 Parts of the compound (1a) or the compound (1b), 1 part of metconazole, 3 parts of calcium lignin sulfonate, 2 parts of sodium lauryl sulfate and 54 parts of synthetic hydrated silicon oxide are fully ground and mixed so as to obtain respective wettable powders.

Seed Treatment Example 1

An emulsion prepared as in Formulation example 1 is used for smear treatment in an amount of 500 ml per 100 kg of dried sorghum seeds using a rotary seed treatment machine (seed dresser, produced by Hans-Ulrich Hege GmbH) so as to obtain treated seeds.

Seed Treatment Example 2

A flowable prepared as in Formulation example 16 is used for smear treatment in an amount of 50 ml per 10 kg of dried rape seeds using a rotary seed treatment machine (seed dresser, produced by Hans-Ulrich Hege GmbH) so as to obtain treated seeds.

Seed Treatment Example 3

A flowable prepared as in Formulation example 17 is used for smear treatment in an amount of 40 ml per 10 kg of dried corn seeds using a rotary seed treatment machine (seed dresser, produced by Hans-Ulrich Hege GmbH) so as to obtain treated seeds.

Seed Treatment Example 4

5 Parts of a flowable agent prepared as in Formulation example 18, 5 parts of pigment BPD6135 (manufactured by Sun Chemical) and 35 parts of water are mixed to prepare a mixture. The mixture is used for smear treatment in an amount of 60 ml per 10 kg of dried rice seeds using a rotary seed treatment machine (seed dresser, produced by Hans-Ulrich Hege GmbH) so as to obtain treated seeds.

Seed Treatment Example 5

A powder agent prepared as in Formulation example 19a is used for powder coating treatment in an amount of 50 g per 10 kg of dried corn seeds so as to obtain treated seeds.

Seed Treatment Example 6

An emulsion prepared as in Formulation example 22 is used for smear treatment in an amount of 500 ml per 100 kg of dried sugar beet seeds using a rotary seed treatment machine (seed dresser, produced by Hans-Ulrich Hege GmbH) so as to obtain treated seeds.

Seed Treatment Example 7

A flowable prepared as in Formulation example 23 is used for smear treatment in an amount of 50 ml per 10 kg of dried soy bean seeds using a rotary seed treatment machine (seed dresser, produced by Hans-Ulrich Hege GmbH) so as to obtain treated seeds.

Seed Treatment Example 8

A granule agent prepared as in Formulation example 24 is used for smear treatment in an amount of 50 ml per 10 kg of dried wheat seeds using a rotary seed treatment machine (seed dresser, produced by Hans-Ulrich Hege GmbH) so as to obtain treated seeds.

Seed Treatment Example 9

5 Parts of a wettable powder prepared as in Formulation example 25, 5 parts of pigment BPD6135 (manufactured by Sun Chemical) and 35 parts of water are mixed and the resultant mixture is used for smear treatment in an amount of 70 ml per 10 kg of potato tuber pieces using a rotary seed treatment machine (seed dresser, produced by Hans-Ulrich Hege GmbH) so as to obtain treated seeds.

Seed Treatment Example 10

A wettable powder prepared as in Formulation example 20 is used for powder coating treatment in an amount of 40 g per 10 kg of dried cotton seeds so as to obtain treated seeds.

Test Example 1

A plastic pot was filled with sandy soil, and cucumber (Sagamihanjiro) was then disseminated. The cucumber was allowed to grow in a green house for 12 days. A wettable powder of the compound (1b) and a commercially available metconazole formulation (Caramba (registered trademark) produced by BASF) were respectively diluted with water and then tank-mixed so as to prepare tank-mixed liquids containing compound (1b) and metconazole in predetermined concentration. The tank-mixed liquids were subjected to foliage application such that they could be sufficiently adhered to the leaves of the aforementioned cucumber plants. After completion of the foliage application, the plants were air-dried. Thereafter, a PDA nutrient medium containing spores of *Botrytis cinerea*, pathogen of gray mold of cucumber, was placed onto the leaf surface of the cucumber plants. They were placed at 12° C. under high humidity for 6 days after the inoculation, and thereafter control effect was checked. The diameter of infected area on the plants on which the agents had been sprayed was determined as the incidence of disease at the time of checking and the control value was calculated by Equation 1 based on the incidence of disease thus determined.

As a comparison, the respective wettable powders described above were diluted with water in predetermined concentration so as to prepare a compound (1b) liquid and a metconazole liquid respectively and they were subjected to similar disease control test. Besides, in order to calculate the control value, the incidence of disease was also determined in the case in which the plants had not been treated with the agent.

The results are shown in Table 2.

$$\text{Control value} = 100(A-B)/A \qquad \text{``Equation 1'';}$$

A: Incidence of disease of plant or planted area in untreated area

B: Incidence of disease of plant or planted area in treated area

Generally, the control value expected for the case where the given two kinds of active ingredient compounds are mixed and used for the treatment, the so-called control value expectation is calculated from the following Colby's calculating equation.

$$E = X+Y-(X \times Y)/100 \qquad \text{``Equation 2'';}$$

X: Control value (%) when active ingredient compound A is used for treatment in M ppm, in M g per 100 kg of seeds or in M g per 1 hectare Y: Control value (%) when active ingredient compound B is used for treatment in N ppm, in N g per 100 kg of seeds or in N g per 1 hectare E: Control value (%) expected for the case in which active ingredient compound A in M ppm, in M g per 100 kg of seeds or in M g per 1 hectare and active ingredient compound B in N ppm, in N g per 100 kg of seeds or in N g per 1 hectare are mixed and used for treatment (hereinbelow referred to as "control value expectation")

"Synergetic effect(%)"=(Actual control value)×100/(Control value expectation)

TABLE 2

| Compound (1b) | Metconazole | Actual control value | Control value expectation | Synergistic effect (%) |
| --- | --- | --- | --- | --- |
| 0.2 ppm | 0.8 ppm | 33 | 23 | 144 |
| 0.2 ppm | 0 ppm | 16 | — | — |
| 0 ppm | 0.8 ppm | 8 | — | — |

Test Example 2

Mixed liquids containing an acetone solution of compound (1b) and an acetone solution of metconazole were prepared.

These mixed liquids were used for smear treatment of cucumber (Sagamihanjiro) seeds using a rotary seed treatment machine (seed dresser, produced by Hans-Ulrich Hege GmbH) so as to obtain treated seeds. The treated seeds were left untouched overnight and then disseminated on the soil filled in a plastic pot and covered with the soil containing *Rhizoctonia solani*, pathogen of cucumber damping-off, which had been cultured on a bran medium. They were allowed to grow in a greenhouse while irrigated and the number of non-budding seeds was checked on the seventh day after the dissemination and the incidence of disease was calculated by Equation 3. The control value was calculated by the aforementioned Equation 1 based on the incidence of disease. As a comparison, acetone solutions containing the compound (1b) and metconazole respectively in the predetermined concentration were prepared and subjected to similar tests.

The results are shown in Table 3.

Incidence of disease=(Number of no budding seeds)×
100/(Number of total disseminated seeds)    "Equation 3";

TABLE 3

| Compound (1b) | Metconazole | Actual control value | Control value expectation | Synergistic effect (%) |
|---|---|---|---|---|
| 1 g/100 kg-seed | 1 g/100 kg-seed | 83 | 69 | 120 |
| 1 g/100 kg-seed | 0 g/100 kg-seed | 30 | — | — |
| 0 g/100 kg-seed | 1 g/100 kg-seed | 39 | — | — |

Test Example 3

A plastic pot was filled with sandy soil, and cucumber (Sagamihanjiro) was then disseminated. The cucumber was allowed to grow in a green house for 12 days. A wettable powder of the compound (1b) and a commercially available ipconazole formulation (Techlead wettable powder produced by Kureha Corporation) were respectively diluted with water and then tank-mixed so as to prepare tank-mixed liquids containing the compound (1b) and the ipconazole in predetermined concentration. The tank-mixed liquids were subjected to foliage application such that they could be sufficiently adhered to the leaves of the aforementioned cucumber plants. After completion of the foliage application, the plants were air-dried. Thereafter, a PDA nutrient medium containing spores of *Botrytis cinerea*, pathogen of gray mold of cucumber, was placed onto the leaf surface of the cucumber plants. They were placed at 12° C. under high humidity for 6 days after the inoculation, and thereafter control effect was checked. The diameter of infected area on the plants on which the agents had been sprayed was determined as the incidence of disease at the time of checking and the control value was calculated by the aforementioned Equation 1 based on the incidence of disease thus determined.

As a comparison, the respective wettable powders described above were diluted with water in predetermined concentration so as to prepare a compound (1b) liquid and an ipconazole liquid respectively and they were subjected to similar disease control test. Besides, in order to calculate the control value, the incidence of disease was also determined in the case in which the plants has not been treated with the agent.

The results are shown in Table 4.

TABLE 4

| Compound (1b) | Ipconazole | Actual control value | Control value expectation | Synergistic effect (%) |
|---|---|---|---|---|
| 0.2 ppm | 3.1 ppm | 29 | 20 | 147 |
| 0.2 ppm | 0 ppm | 8 | — | — |
| 0 ppm | 3.1 ppm | 13 | — | — |

Test Example 4

An acetone solution of the compound (1b) and an acetone solution of ipconazole were mixed to prepare mixed liquids containing the compound (1b) and ipconazole in predetermined concentration. These mixed liquids were used for smear treatment of cucumber (Sagamihanjiro) seeds using a rotary seed treatment machine (seed dresser, produced by Hans-Ulrich Hege GmbH) so as to obtain treated seeds. The treated seeds were left untouched overnight and then disseminated on the soil filled in a plastic pot and covered with the soil containing *Rhizoctonia solani*, pathogen of cucumber damping-off, which had been cultured on a bran medium. They were allowed to grow in a greenhouse while irrigated and the number of non-budding seeds was checked on the seventh day after the dissemination and the incidence of disease was calculated by the aforementioned Equation 3. The control value was calculated by the aforementioned Equation 1 based on the incidence of disease. In order to calculate the control value, the incidence of disease was also determined in the case in which the plants had not been treated with the agent.

As a comparison, acetone solutions containing the compound (1b) and ipconazole respectively in the predetermined concentration were prepared and subjected to similar tests.

TABLE 5

| Compound (1b) | Ipconazole | Actual control value | Control value expectation | Synergistic effect (%) |
|---|---|---|---|---|
| 1 g/100 kg-seed | 1 g/100 kg-seed | 74 | 61 | 122 |
| 1 g/100 kg-seed | 0 g/100 kg-seed | 30 | — | — |
| 0 g/100 kg-seed | 1 g/100 kg-seed | 30 | — | — |

Test Example 5

A plastic pot was filled with sandy soil, and turf (Bent grass Penncross) was then disseminated. The turf was allowed to grow in a green house for 20 days. A wettable powder of the compound (1b) and a commercially available metconazole formulation (Caramba (registered trademark) produced by BASF) were respectively diluted with water and then tank-mixed so as to prepare tank-mixed liquids containing the compound (1b) and the metconazole in predetermined concentration. The tank-mixed liquids were subjected to foliage application such that they could be sufficiently adhered to the leaves of the aforementioned turf plants. After completion of the foliage application, the plants were air-dried. Thereafter, bran medium containing mycelium of *Rhizoctonia solani*, pathogen of brown patch of turf, was sprinkled over the planted area. They were placed at 12° C.-23° C. under high humidity for 10 days after the inoculation, and thereafter control effect was checked. The diameter of infected area on the planted area on which the agents had been sprayed was determined as the incidence of disease at the time of checking and the control value was calculated by the aforementioned Equation 1 based on the incidence of disease determined.

As a comparison, the respective wettable powders described above were diluted with water in predetermined concentration so as to prepare a compound (1b) liquid and a metconazole liquid respectively and they were subjected to similar disease control test. Besides, in order to calculate the control value, the incidence of disease was also determined in the case in which the plants had not been treated with the agent.

The results are shown in Table 6.

TABLE 6

| Compound (1b) | Metconazole | Actual control value | Control value expectation | Synergistic effect (%) |
|---|---|---|---|---|
| 600 g/ha | 37.5 g/ha | 100 | 73 | 136 |
| 600 g/ha | 9.4 g/ha | 100 | 73 | 136 |
| 600 g/ha | 0 g/ha | 88 | — | — |
| 0 g/ha | 37.5 g/ha | 63 | — | — |
| 0 g/ha | 9.4 g/ha | 63 | — | — |

INDUSTRIAL APPLICABILITY

According to the present invention, a composition for controlling plant diseases having high activity, and a method for effectively controlling plant diseases can be provided.

The invention claimed is:

1. A composition for controlling plant diseases comprising, as active ingredients, a compound represented by formula (1):

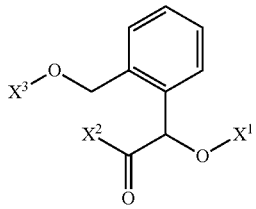

(1)

wherein $X^1$ represents a methyl group; $X^2$ represents a methylamino group; and $X^3$ represents a 2,5-dimethylphenyl group;
and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole.

2. The composition according to claim 1, wherein the azole compound is at least one azole compound selected from the group consisting of bromuconazole, difenoconazole, fluquinconazole, ipconazole, prothioconazole, tetraconazole, triticonazole and metconazole.

3. The composition according to claim 2, which has a weight ratio of the compound represented by formula (1) to the at least one azole compound falling within the range of from 0.0125:1 to 500:1.

4. The composition according to claim 1, which has a weight ratio of the compound represented by formula (1) to the at least one azole compound falling within the range of from 0.0125:1 to 500:1.

5. A seed treatment agent comprising, as active ingredients, the compound represented by formula (1):

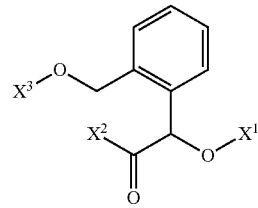

(1)

wherein $X^1$ represents a methyl group; $X^2$ represents a methylamino group; and $X^3$ represents a 2,5-dimethylphenyl group;
and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole.

6. A plant seed treated with effective amounts of the compound represented by formula (1):

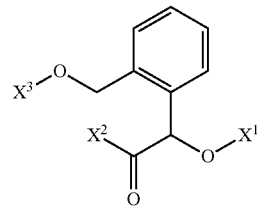

(1)

wherein $X^1$ represents a methyl group; $X^2$ represents a methylamino group; and $X^3$ represents a 2,5-dimethylphenyl group;
and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole.

7. A method for controlling plant diseases which comprises applying, to a plant or a locus where a plant is allowed to grow, effective amounts of the compound represented by formula (1):

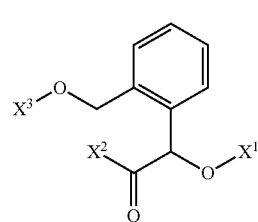

(1)

wherein $X^1$ represents a methyl group; $X^2$ represents a methylamino group; and $X^3$ represents a 2,5-dimethylphenyl group;
and at least one azole compound selected from the group consisting of bromuconazole, cyproconazole, difenoconazole, fenbuconazole, fluquinconazole, hexaconazole, imibenconazole, ipconazole, myclobutanil, prothioconazole, simeconazole, tetraconazole, triticonazole and metconazole.

* * * * *